United States Patent [19]

Inaba et al.

[11] Patent Number: 5,035,865

[45] Date of Patent: Jul. 30, 1991

[54] VACUUM BLOOD SAMPLE COLLECTING DEVICE

[75] Inventors: Fumiaki Inaba; Satoshi Inoue, both of Fujinomiya, Japan

[73] Assignee: Terumo Kabushiki Kaisha, Tokyo, Japan

[21] Appl. No.: 352,097

[22] Filed: May 15, 1989

[30] Foreign Application Priority Data

| May 17, 1988 | [JP] | Japan | 63-118245 |
| May 17, 1988 | [JP] | Japan | 63-118246 |
| May 17, 1988 | [JP] | Japan | 63-118248 |

[51] Int. Cl.$^5$ .................. G05D 16/00; A61M 1/00
[52] U.S. Cl. ............................ 422/99; 422/112; 604/319; 604/320; 604/119; 604/146
[58] Field of Search ............ 422/68.1, 82.13, 100, 422/112, 99; 604/317, 319, 320

[56] References Cited

U.S. PATENT DOCUMENTS

| 3,098,480 | 11/1960 | Worthington | 604/4 |
| 4,127,111 | 11/1978 | Drolet | 422/68.1 |
| 4,184,510 | 1/1980 | Murry et al. | 604/22 |
| 4,231,366 | 11/1980 | Schael | 604/4 |
| 4,648,385 | 3/1987 | Oumi et al. | 600/17 |
| 4,795,448 | 1/1989 | Stacey et al. | 604/319 |
| 4,888,003 | 12/1989 | Johnson et al. | 604/319 |

FOREIGN PATENT DOCUMENTS 2603190 3/1988 France .................. 604/317

Primary Examiner—Robert J. Warden
Assistant Examiner—Theresa A. Trembley
Attorney, Agent, or Firm—Frishauf, Holtz, Goodman & Woodward

[57] ABSTRACT

A blood sample collecting device includes a vacuum blood sampling chamber having a blood container disposed therein, and a vacuum pump for evacuating the vacuum blood sampling chamber to collect a blood sample into the blood container under a vacuum developed in the vacuum blood sampling chamber. The amount of collected blood in the blood container, and the vacuum in the vacuum blood sampling chamber is lowered below a preset pressure on the condition that a rate of increase in the measured amount of collected blood does not reach a predetermined normal rate of increase.

17 Claims, 10 Drawing Sheets

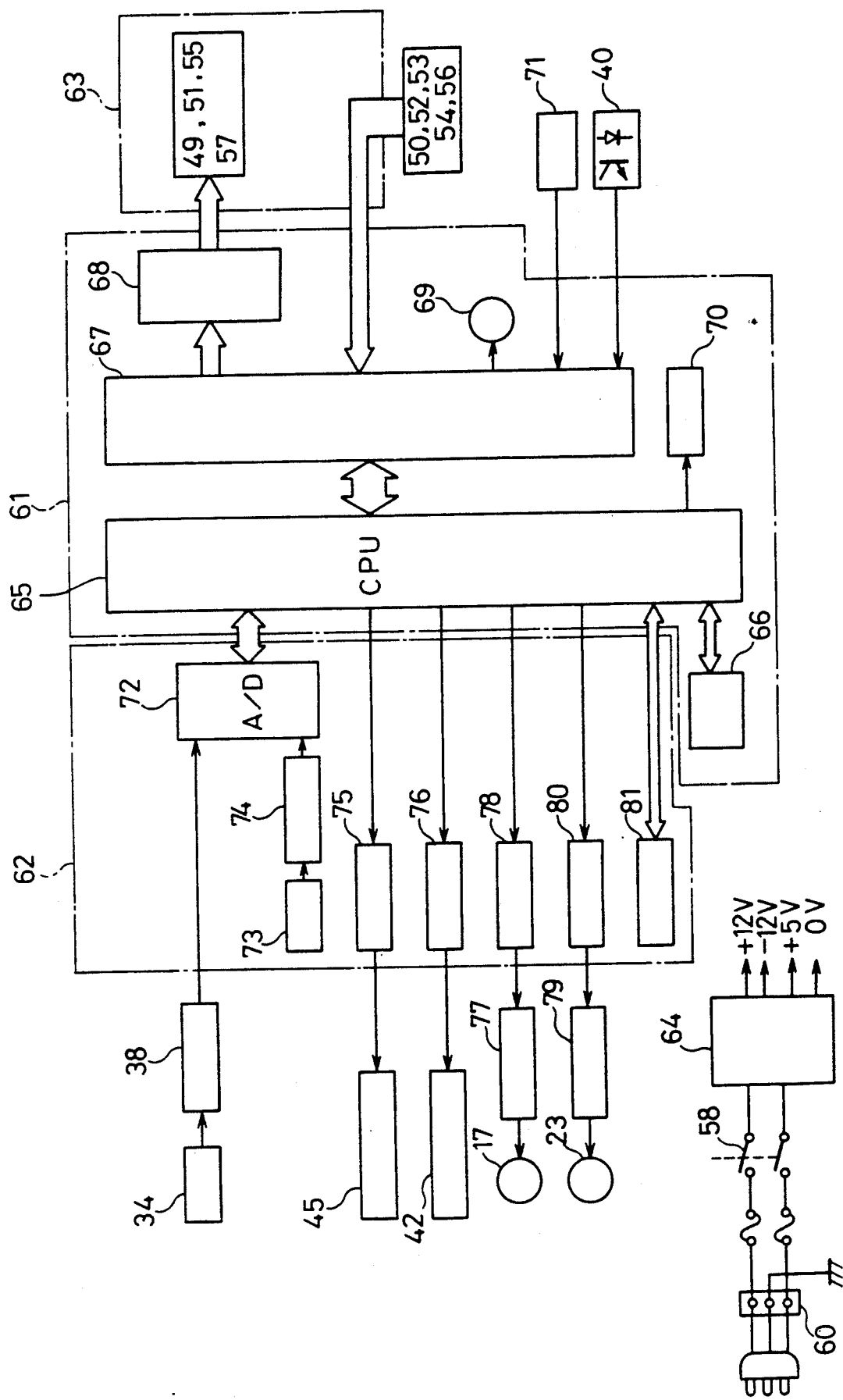

VACUUM BLOOD SAMPLE COLLECTING DEVICE

BACKGROUND OF THE INVENTION

The present invention relates to a vacuum blood sample collecting device for collecting a blood sample in a blood container.

One known vacuum blood sample collecting device is disclosed in Japanese Patent Publication No. 51-3153. The disclosed vacuum blood sampler has a blood container disposed in a vacuum blood sampling chamber which is evacuated by a vacuum pump. The vacuum pump develops a vacuum that acts in the blood container to produce a suction force in a blood sampling needle connected to the blood container through a tube or the like for thereby drawing blood from a blood vessel in a blood donor or patient. The vacuum or negative pressure after the blood starts being sampled is required to be kept at a suitable level for facilitating the blood sampling operation and reducing the burden on the blood donor. To regulate the pressure in the vacuum blood sampling chamber to an adequate level, a pressure regulating valve is disposed in a vacuum pipe which interconnects the vacuum pump and the vacuum blood sampling chamber. When the pressure in the vacuum blood sampling chamber reaches a desired target level, a spring-loaded leakage mechanism in the pressure regulating valve is operated to keep the pressure in the vacuum blood sampling chamber at the target level.

With the above prior arrangement, even after the pressure in the vacuum blood sampling chamber has reached the target level, the vacuum pump is continuously operated. Therefore, the vacuum blood sampler is of poor electric efficiency and generates heat. During operation of the vacuum blood sampler over a relatively long period of time, the seals and spring of the leakage mechanism in the pressure regulating valve are deteriorated to vary a control pressure, thus making it difficult to maintain the desired target pressure in the vacuum blood sampling chamber. The desired target pressure cannot easily be varied and set since it is controlled by a skilled operator through adjustment of the resiliency of the spring of the leakage mechanism.

When the vacuum level is quickly lowered toward a final target level, the force tending to draw blood from the blood vessel is rapidly varied to put an excessive burden on the blood donor, and a blood vessel wall is attracted to the blood sampling needle under the large suction force developed in the hole of the blood sampling needle. If the blood vessel in the blood donor is narrower than normal, the needle hole may be closed by the blood vessel wall, making it difficult or impossible to effect continued blood sampling operation. Accordingly, the efficiency of blood sampling is lowered.

SUMMARY OF THE INVENTION

It is a first object of the present invention to provide a vacuum blood sample collecting device capable of stably sampling blood from blood vessels of different diameters.

It is a second object of the present invention to provide a vacuum blood sample collecting device which can develop a constant vacuum in a vacuum blood sampling chamber with increased electric efficiency, can maintain a stably controlled vacuum in the vacuum blood sampling chamber over a long period of time, and can easily vary the level of a vacuum developed in the vacuum blood sampling chamber.

It is a third object of the present invention to provide a vacuum blood sampler which reduces the burden on a blood donor or patient and increases the efficiency of blood sampling operation while a blood sample is being collected into a blood container under a vacuum developed in a vacuum blood sampling chamber.

Another object of the present invention is to provide a blood sample collecting device comprising: a vacuum blood sampling chamber having a blood container disposed therein; a vacuum pump for evacuating the vacuum blood sampling chamber to collect a blood sample into the blood container under a vacuum developed in said vacuum blood sampling chamber; measuring means for measuring the amount of collected blood in said blood container; and control means for lowering the vacuum in said vacuum blood sampling chamber below a preset pressure on the condition that a rate of increase in the measured amount of collected blood does not reach a predetermined normal rate of increase.

Still another object of the present invention is to provide a blood sample collecting device comprising: a vacuum blood sampling chamber having a blood container disposed therein; a vacuum pump for evacuating the vacuum blood sampling chamber to collect a blood sample into the blood container under a vacuum developed in said vacuum blood sampling chamber; a pressure sensor for detecting the pressure in said vacuum blood sampling chamber; memory means for storing a preset pressure to be developed in said vacuum blood sampling chamber; and control means responsive to the pressure detected by said pressure sensor and the preset pressure stored in said memory means for turning on and off said vacuum pump so that the pressure detected by said pressure sensor will coincide with the preset pressure stored in said memory means.

A further object of the present invention is to provide a blood sample collecting device comprising: a vacuum blood sampling chamber having a blood container disposed therein; a vacuum pump for evacuating the vacuum blood sampling chamber to collect a blood sample into the blood container under a vacuum developed in said vacuum blood sampling chamber; measuring mean for measuring the amount of collected blood in said blood container; and control means for controlling a rate of increase in the measured amount of collected blood during a blood collecting cycle.

The above and other objects, features and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 7 is a detailed block diagram of a controller in the vacuum blood sample collecting device shown in FIG. 1;

DETAILED DESCRIPTION OF THE PREFERRED EMBODIMENT

Figure 1:
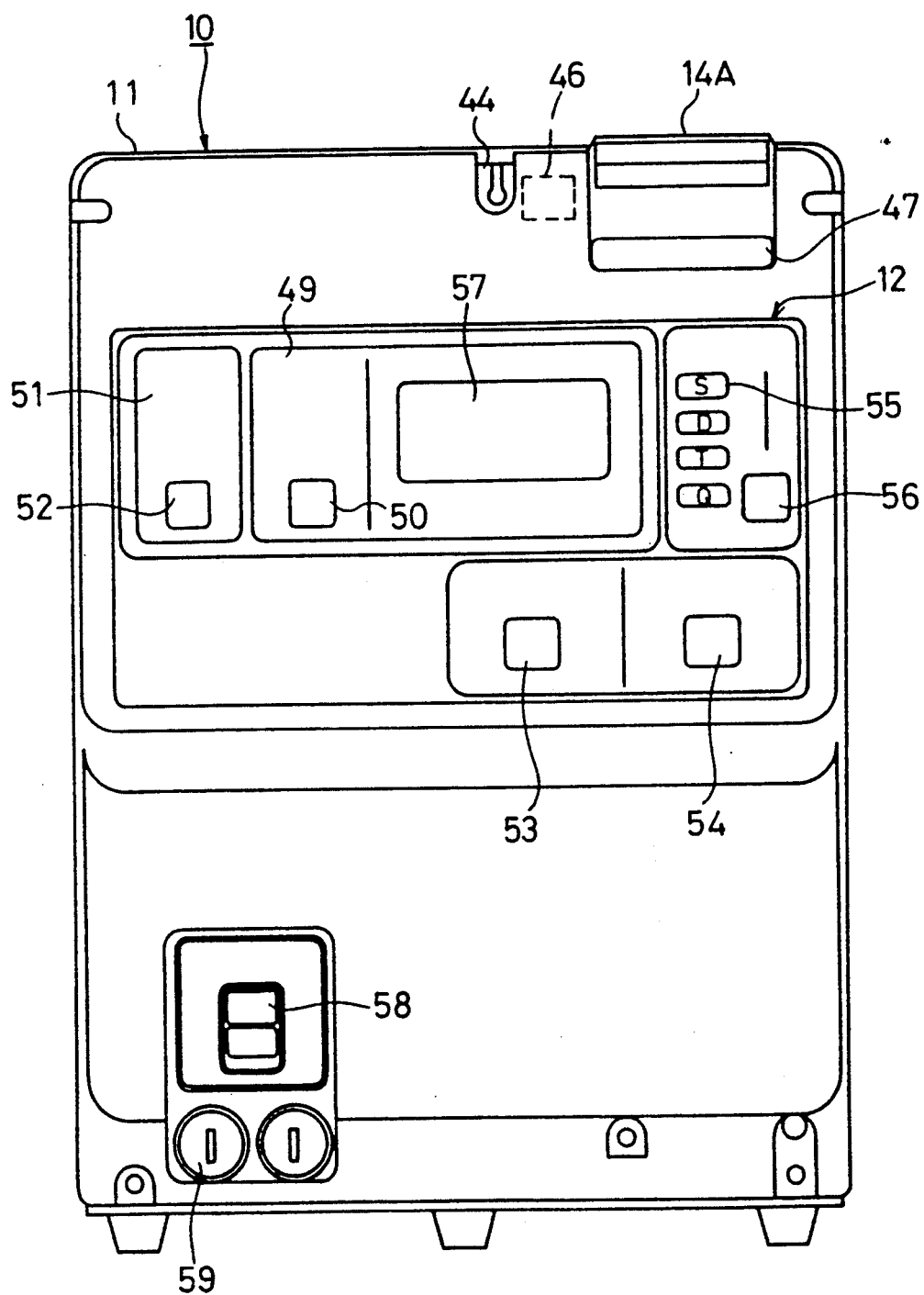
FIG. 1 is a front elevational view of a vacuum blood sample collecting device according to the present invention.
Figure 2:
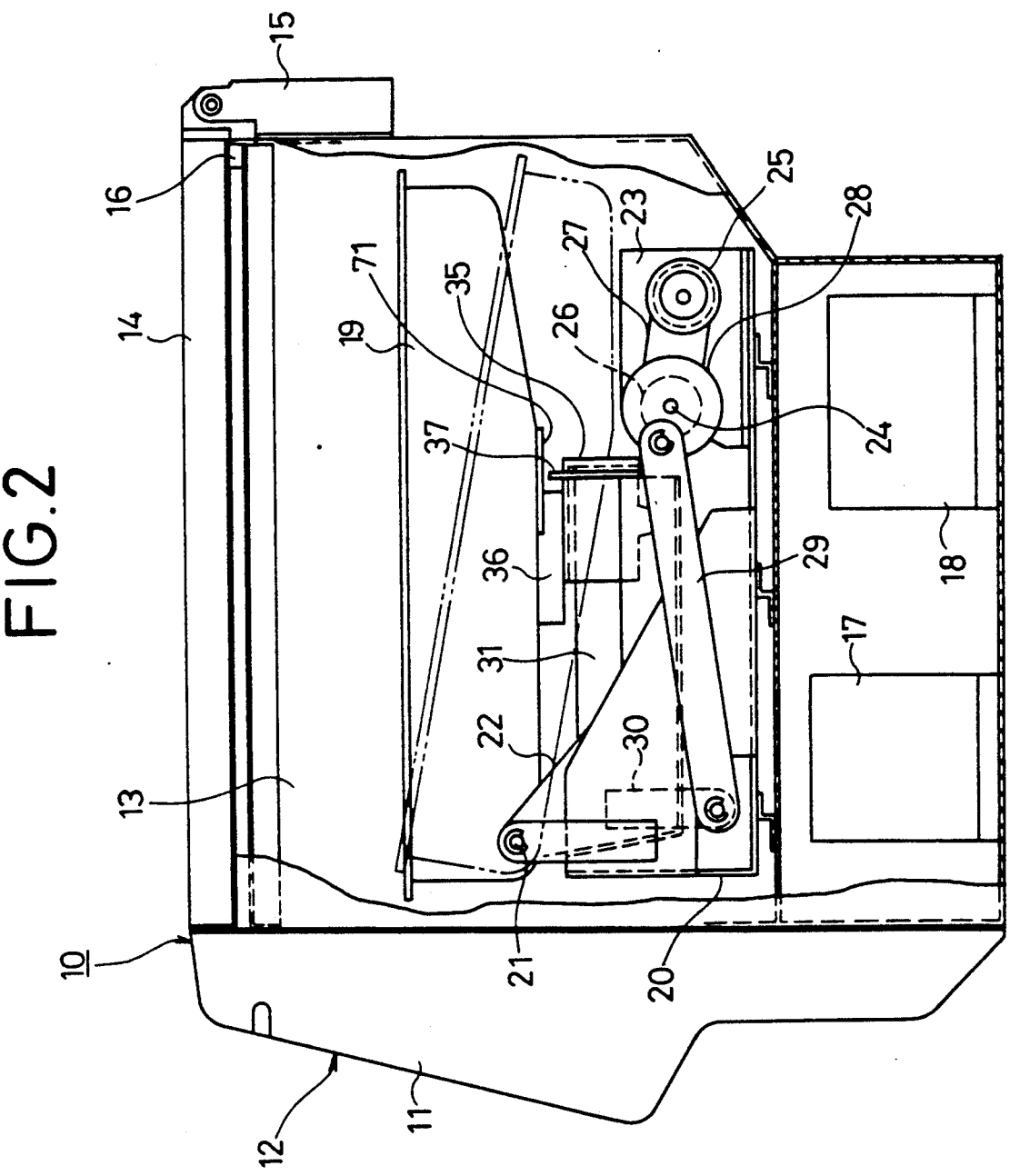
FIG. 2 is a side elevational view of an internal mechanism of the vacuum blood sample collecting device shown in FIG. 1.
Figure 3:
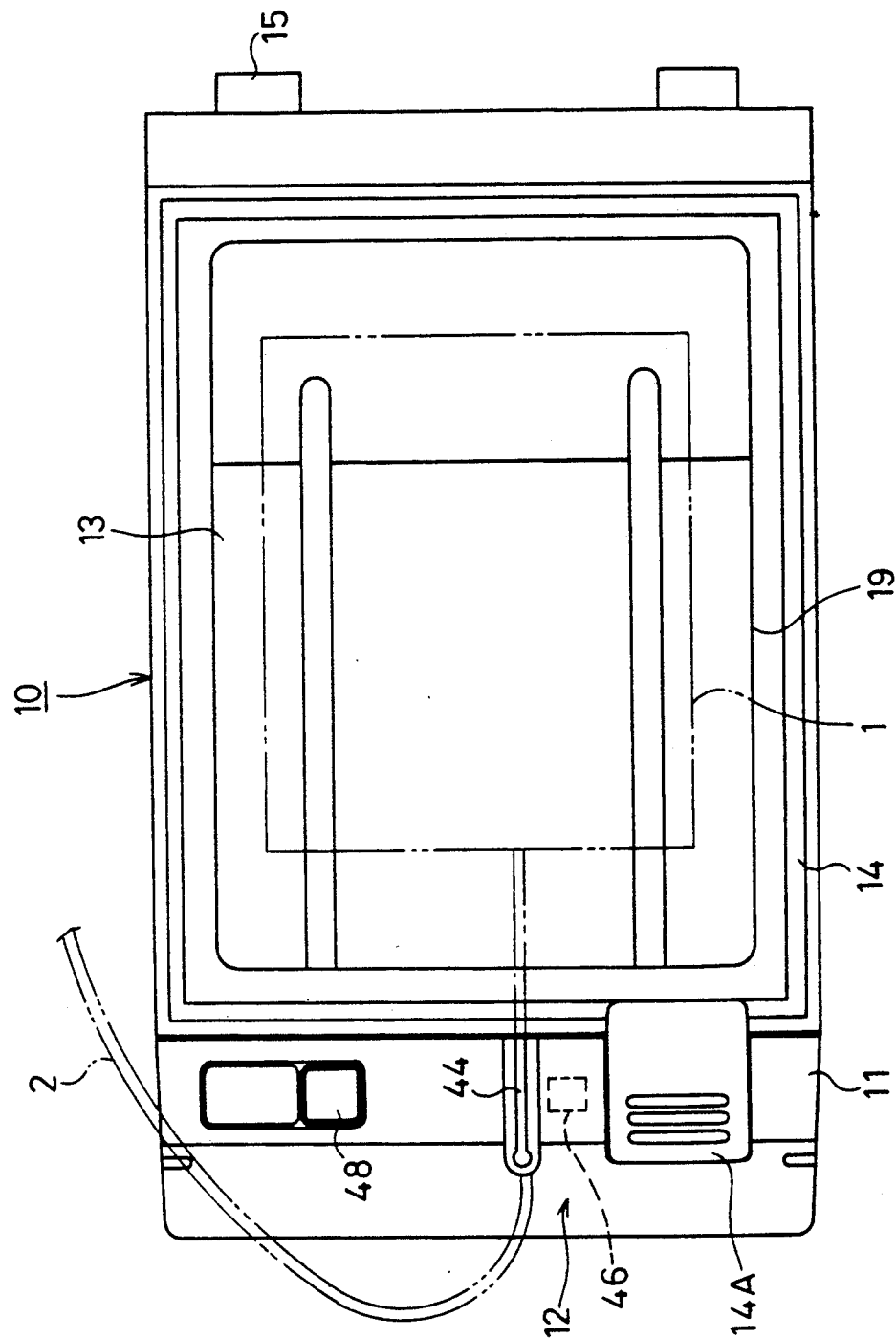
FIG. 3 is a plan view of the vacuum blood sample collecting device illustrated in FIG. 1.

FIGS. 1 through 7 show a vacuum blood sample collecting device 10 according to the present invention. The vacuum blood sample collecting device 10 has a display panel 12 (FIG. 1) on the front wall of a housing 11 which accommodates a vacuum blood sampling chamber 13 (FIGS. 2, 3, and 4) therein. The vacuum blood sampling chamber 13 can be opened and closed by a cover 14 pivotally mounted on the housing 11 by means of hinges 15. The vacuum blood sampling chamber 13 is sealed by a rubber seal 16. The cover 14 has a grip 14A (FIG. 1) which is to be gripped by the operator when the cover 14 is to be opened and closed The vacuum blood sample collecting device 10 also has a vacuum pump 17 and a controller 18 disposed in a lower portion of the housing 11, as shown in FIG. 2.

The vacuum blood sampling chamber 13 communicates with an inlet port 17A (FIG. 6) of the vacuum pump 17 and can be evacuated by the vacuum pump 17. The vacuum blood sampling chamber 13 houses a bag tray 19 (FIGS. 2, 3, and 4) for supporting a blood bag (blood container) 1 which is made of polyvinyl chloride or the like. When the vacuum blood sampling chamber 13 is evacuated, a predetermined vacuum is developed on the blood bag 1 supported on the bag tray 19 for collecting a blood sample into the blood bag 1. While blood is being sampled into the blood bag 1, the bag tray 19 is oscillated back and forth to agitate the collected blood and an anticoagulant such as heparin which has been placed in the blood bag 1, and at the same time measures the weight of the blood bag 1 containing collected blood.

A mechanism for oscillating the bag tray 19 and a mechanism for measuring the weight of the collected blood in the blood bag 1 will be described below.

Figure 4:
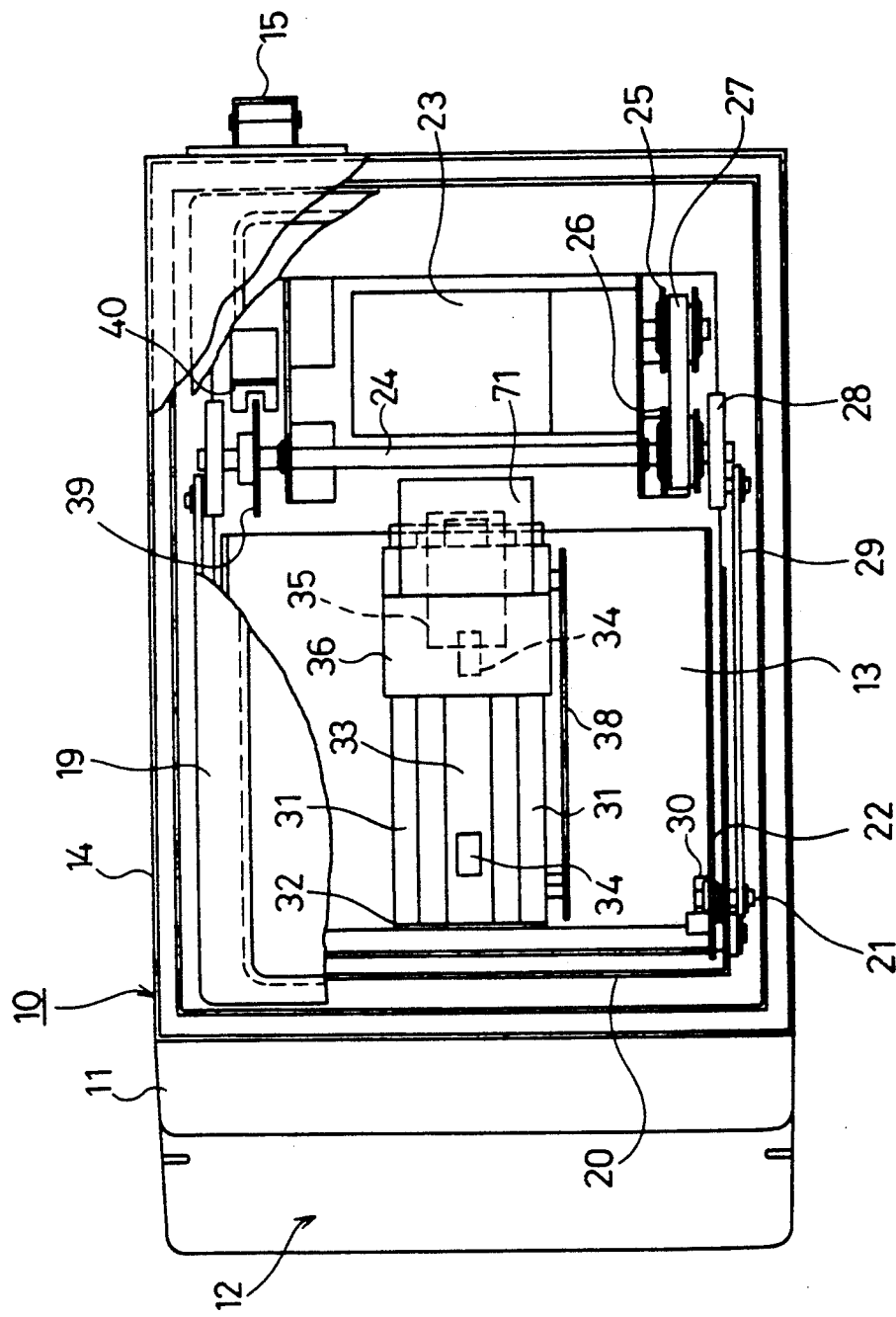
FIG. 4 is a plan view of the internal mechanism of the vacuum blood sample collecting device shown in FIG. 1.
Figure 5:
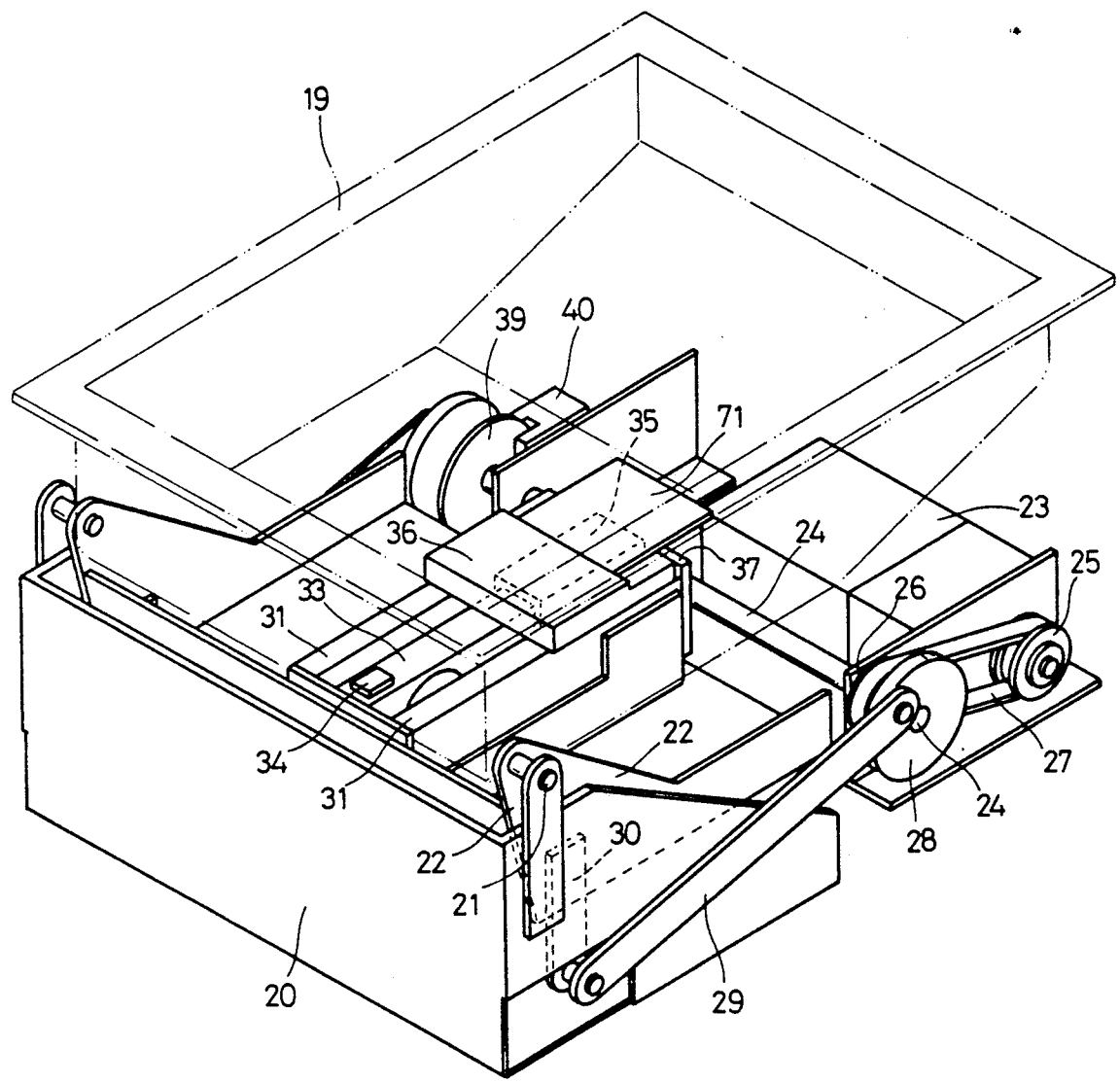
FIG. 5 is a perspective view of the internal mechanism of the vacuum blood sample collecting device shown in FIGS. 1 through 4.

As shown in FIGS. 2, 4, and 5, a mount base 20 is disposed on the bottom wall of the vacuum blood sampling chamber 13. An oscillating frame 22 which is swingable is supported on the mount base 20 by means of support shafts 21 which are pivotally supported on arms fixed to the mount base 20. An oscillating motor 23 is fixedly mounted on the mount base 20 and has a drive shaft 24 on which a toothed pulley 25 is mounted. A toothed belt 27 is trained around the pulley 25 and another toothed pulley 26 mounted on a drive shaft 24. On one end of the drive shaft 24, there is mounted a crank wheel 28 having an eccentric pin coupled to one end of a link 29, the other end of which is coupled by a pin to a connector 30 integrally joined to the oscillating frame 22.

A pair of scale attachment blocks 31 is fixed to the upper surface of the oscillating frame 22, and a scale (means for measuring the amount of collected blood) 33 is supported in a cantilevered fashion on a support plate 32 attached to ends of the scale attachment blocks 31. The scale 33 has a pair of strain gages 34 attached to the upper surface thereof at two respective positions and serving as weight sensors constituting a Wheatstone bridge. The bag tray 19 is fixedly mounted on the distal end of the scale 33 through a weighing base 35 and a receiver plate 36. The scale 33 is prevented by a stopper 37 from jiggling laterally. An amplifier unit 38 is electrically connected to the weight sensors or strain gages 34.

When the oscillating motor 23 is energized, the drive shaft 24 and the crank wheel 28 are rotated through the pulley 25, the toothed belt 27, and the pulley 26 to displace the link 29 for thereby oscillating the oscillating frame 22 about the support shafts 21. Therefore, the bag tray 19 supported on the oscillating frame 22 through the scale 33 is also oscillated The bag tray 19 is supported on the scale 33 which is supported in a cantilevered manner on the oscillating frame 22 through the attachment blocks 31 and the support plate 32. The weight of the blood bag 1 containing collected blood is measured according to the flexural deformation of the scale 33, and the amount of collected blood is calculated from the measured weight.

The angular position of a detector cam 39 mounted on the other end of the drive shaft 24 is detected by an optical sensor 40. In response to a detected signal from the optical sensor 40, the oscillating motor 23 is controlled to temporarily stop the bag tray 19 in its lowermost position (bottom dead center) and keep the bag tray 19 in a certain attitude while at the same time the weight of the blood bag 1 is measured.

Figure 6:
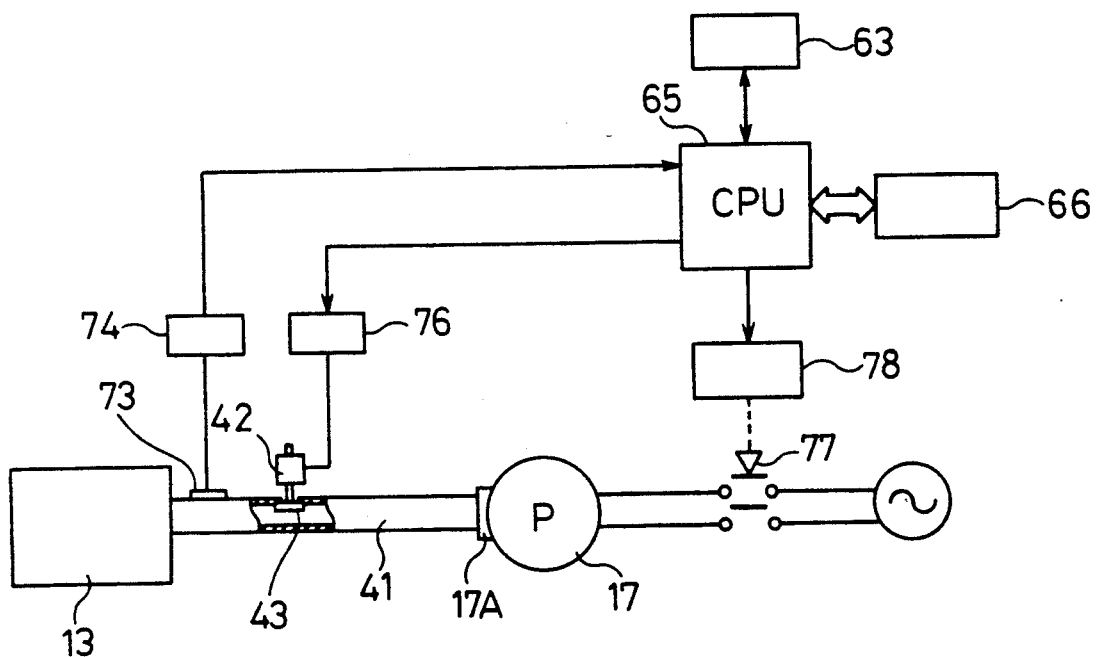
FIG. 6 is a block diagram of a vacuum circuit and a control system in the vacuum blood sample collecting device.

As shown in FIG. 6, the inlet port 17A of the vacuum pump 17 and the vacuum blood sampling chamber 13 are connected to each other by means of a vacuum pipe 41 which has a discharge valve 43 that can be closed when a discharge solenoid 42 is turned on and opened by gravity when the discharge solenoid 42 is turned off. By actuating the vacuum pump 17, a certain vacuum is developed in the vacuum blood sampling chamber 13 to collect a blood sample. After the blood sample has been collected, the discharge valve 43 is opened to vent the vacuum blood sampling chamber 13 to atmosphere.

A tube holder 44 (FIG. 3) is disposed on an upper portion of the front wall of the housing 11 and adjacent to the vacuum blood sampling chamber 13. A blood sampling tube 2 connected to the blood bag 1 housed in the vacuum blood sampling chamber 13 can be pulled through the tube holder 44. The tube holder 44 is associated with a tube clamp (blood sampling stop means) 46 which is actuatable by a tube clamp solenoid 45. The tube clamp 46 serves to clamp and close the blood sampling tube 2 to stop the flow of sampled blood into the blood bag 1. The tube clamp 46 can be released by depressing a tube unclamping button 47, and can be operated in an emergency by a tube clamping button 48.

The display panel 12 has an amount-of-blood/vacuum selector lamp 49, an amount-of-blood/vacuum selector switch 50, a 400 ml/200 ml selector lamp 51, a 400 ml/200 ml selector switch 52, a stop switch 53, a start switch 54, a bag indication lamp 55, a bag selector switch 56, and an amount-of-blood/vacuum display 57. The vacuum blood sample collecting device 10 also has a power supply switch 58 and a fuse holder 59 on a lower portion of the front wall of the housing 11, and a power supply connector 60 on a lower portion of the rear wall of the housing 11.

The controller 18 of the vacuum blood sample collecting device 10 will be described below. As shown in FIG. 7, the control unit 18 generally comprises a main control circuit 61, a driver circuit 62, and a display circuit 63.

The main control circuit 61 includes a CPU (central processing unit) 65, a memory 66, an input/output control unit 67, a LED (light-emitting diode) driver 68, a buzzer 69, and a fail-safe control circuit 70. The input/output control unit 67 is supplied with a detected signal from the optical sensor 40 which detects the angular position of the bag tray 19, and a detected signal from a blood leakage sensor 71 which detects a blood leakage from the blood bag 1.

The memory 66 comprises a nonvolatile memory such as an EA-ROM, EEP-ROM, or the like. Data stored in the memory 66 can be rewritten and read out, and remains stored even when there is no power supply voltage applied thereto. The data stored in the memory 66 include, for example:

1) the vacuum to be developed in the vacuum blood sampling chamber 13;
2) the amount of blood to be collected in the blood bag 1; and
3) the time for which the bag tray 19 is to be oscillated after a blood sample has been collected.

The buzzer 69 is energized to produce different buzzer sounds when:

1) the collection of a blood sample is completed;
2) the vacuum developed in the vacuum blood sampling chamber 13 is wrong;
3) the oscillating motor 23 rotates erroneously; and
4) the blood leakage sensor 71 detects a blood leakage.

The fail-safe control circuit 70 monitors the CPU 65 for its runaway condition, and de-energizes the vacuum blood sample collecting device 10 safely when CPU 65 suffers from runaway.

The driver circuit 62 is connected to the main control circuit 61 and has an A/D converter 72. To the A/D converter 72, there are connected the amplifier unit 38 and a pressure sensor 73 through an amplifier circuit 74, the pressure sensor 73 being disposed in the vacuum pipe 41 for detecting the vacuum which is developed in the vacuum blood sampling chamber 13.

The driver circuit 62 also includes a solenoid driver 75 for controlling operation of the tube clamp solenoid 45, a solenoid driver 76 for controlling operation of the discharge solenoid 42, a pump driver 78 for turning on and off a power supply switch 77 of the vacuum pump 17, and a motor driver 80 for turning on and off a power supply switch 79 of the oscillating motor 23.

Based on the detected pressure from the pressure sensor 73 and the pressure setting stored in the memory 66 for the pressure in the vacuum blood sampling chamber 13, the CPU 65 turns on or off the power supply switch 77 of the vacuum pump 17 so that the detected pressure will coincide with the preset pressure. The vacuum in the vacuum blood sampling chamber 13 is thus varied within a certain range until it reaches a constant pressure.

The driver circuit 62 also has a mode selector switch 81 for selecting one of various modes of operation of the CPU 65. The modes which can be selected by the mode selector switch 81 include:

1) a first blood sampling mode;
2) a second blood sampling mode;
3) an amount-of-blood setting mode;
4) a vacuum setting mode;
5) a specific gravity setting mode;
6) an extended oscillation time setting mode;
7) a detected weight calibration mode; and
8) a detected pressure calibration mode.

In an embodiment which is designed to achieve the third object described above, 9) a mode for setting a rate of increase in the amount of collected blood is selected.

In the first blood sampling mode, a pre-registered value stored in the memory 66 is read out as an empty weight of a blood bag 1 which is to be used in the present blood sampling cycle, and the amount of collected blood is measured using the pre-registered value. In the second blood sampling mode, the empty weight of a blood bag 1 which is to be used in the present blood sampling cycle is measured, and the amount of blood of collected blood is measured using the measured empty weight. In the amount-of-blood setting mode, the amount of blood to be collected is set to a different amount. In the vacuum setting mode, the vacuum to be developed is set to a different vacuum level In the specific gravity setting mode, the specific gravity of blood to be collected is set to a different specific gravity. In the extended oscillation time setting mode, the extended oscillation time is set to a different time. These settings can be changed by turning on the mode selector switch 81 to display a present setting on the display 57, turning on the stop switch 54 to reduce the setting or turning on the start switch 50 to increase the setting, writing the new setting into the memory 66 by turning on the selector switch 50, and confirming the completion of the writing of the data with the energization of the buzzer 69.

In the detected weight calibration mode, the weight detected by the scale 33 is calibrated. In the detected pressure calibration mode, the pressure detected by the pressure sensor 73 is calibrated.

The display circuit 63 is connected to the main control circuit 61, and has various display elements such as the lamp 49 and various switches such as the selector switch 50 on the display panel 12.

A procedure for collecting a blood sample using the vacuum blood sample collecting device 10 is as follows:

(1) The power supply switch 58 is turned on.

(2) A blood sampling mode is selected, i.e., either the first or second blood sampling mode is selected by the mode selector switch 81.

(3) An amount of blood to be collected is selected by the 400 ml/200 ml selector switch 52. The selected amount is displayed on the selector lamp 51.

(4) A blood bag to be used is selected by the bag selector switch 56, and the selected bag is displayed on the bag indication lamp 55. Blood bags that can be used include a single bag (S) which comprises only a parent bag, a double bag (D) which has one or more small bags, a triple bag (T), and a quadruple bag (Q).

(5) The process of the first blood sampling mode:

(a) A blood sampling needle attached to the end of the blood sampling tube 2 is inserted into a blood vessel in a blood donor or patient, and a certain amount of blood is sampled.

(b) The blood bag 1 is placed in the vacuum blood sampling chamber 13 and put on the bag tray 19, and the blood sampling tube 2 is set in the tube holder 44.

(c) The start switch 54 is turned on. The CPU 65 energizes the vacuum pump 17 and the oscillating motor 23 to evacuate the blood sampling chamber 13 to collect a blood sample and to oscillate the bag tray 13. When the bag tray 19 is temporarily stopped at its lowest position, the CPU 65 detects the amount of collected blood in the blood bag 1 in response to an output signal from the amplifier unit 38, and calculates an amount of blood which is still to be collected, using the preset amount of blood to be collected, the specific gravity of blood, and the pre-registered weight of the blood bag 1, all stored in the memory 66, according to the following equation:

$$\text{The amount of blood to be still collected (ml)} = \quad (1)$$
$$[\text{the preset amount of blood to be collected (g)} +$$
$$\text{the preregistered weight (g)} -$$
$$\text{the amount of collected blood (g)}]/\text{the specific gravity (g/ml)}$$

(d) When the calculated amount of blood to be stilled collected reaches zero, the CPU 55 closes the blood sampling tube 2 with the tube clamp 46 to stop the blood flow into the blood bag 1. At this time, the CPU 65 inactivates the vacuum pump 17 and opens the discharge valve 43 to vent the vacuum blood sampling chamber 13 to atmosphere.

(e) After the blood sample has been collected, the CPU 56 still energizes the oscillating motor 23 over an extended period of time to oscillate the bag tray 19. Thereafter, the buzzer 69 announces the end of the blood sampling process.

(f) The tube unclamping button 47 is turned on, the blood sampling tube 2 is removed from the tube holder 44, and the blood bag 1 is taken out of the vacuum blood sampling chamber 13.

(6) The process of the second blood sampling mode:

(a) The blood bag 1 is placed in the vacuum blood sampling chamber 13 and put on the bag tray 19, and the blood sampling tube 2 is set in the tube holder 44.

(b) A blood sampling needle attached to the end of the blood sampling tube 2 is inserted into a blood vessel in a blood donor or patient.

(c) The start switch 54 is turned on. The CPU 65 measures the empty weight of the blood bag 1 in response to an output signal from the amplifier unit 38, and stores the measured empty weight into the memory 66 (or a memory in the CPU 65).

(d) The start switch 54 is turned on again. The CPU 65 energizes the vacuum pump 17 and the oscillating motor 23 to evacuate the blood sampling chamber 13 to collect a blood sample and to oscillate the bag tray 19. When the bag tray 19 is temporarily stopped at its lowest position, the CPU 65 detects the amount of collected blood in the blood bag 1 in response to an output signal from the amplifier unit 38, and calculates an amount of blood which is still to be collected, using the preset amount of blood to be collected, the specific gravity of blood, and the measured weight of the blood bag 1, all stored in the memory 66, according to the following equation:

$$\text{The amount of blood to be still collected (ml)} = \quad (2)$$
$$[\text{the preset amount of blood to be collected (g)} +$$
$$\text{the measured weight (g)} -$$
$$\text{the amount of collected blood (g)}]/\text{the specific gravity (g/ml)}$$

(e) This step is the same as the step (d) in the above process (5).

(f) This step is the same as the step (e) in the above process (5).

(g) This step is the same as the step (f) in the above process (5).

In both of the above processes 5) and 6), the amount of blood being collected and the vacuum are displayed on the display 57 to allow the operator to monitor the measuring operation. The displayed values can be selected by the selector switch 50.

The vacuum blood sample collecting device 10 which is designed to achieve the first through third objects, described above, is basically constructed as described above. An additional arrangement for achieving the first object, its operation and advantages will be described below.

The vacuum blood sample collecting device 10 has an ability or function to adjust the vacuum level in the vacuum blood sampling chamber 13 as follows:

The CPU 65 of the controller 18:

(a) controls the pressure in the vacuum blood sampling chamber 13 so that the pressure detected by the pressure sensor 73 will be equalized to the preset pressure stored in the memory 66; and (b) reduces the vacuum in the vacuum blood sampling chamber 13 according to the control process (1) or (2), described below, on the condition that the rate of increase in the amount of collected blood measured by the scale 33 does not reach a predetermined normal rate of increase (i.e., the amount of collected blood does not substantially vary) while the pressure detected by the pressure sensor 73 reaches the preset pressure in the memory 66. The rate of increase in the amount of collected blood is indicated by a rate of increase with respect to time, and, in this embodiment, calculated as an increase in the amount of collected blood measured when the bag tray 19 reaches the lowest position in the present oscillating cycle, from the amount of collected blood measured when the bag tray 19 reaches the lowest position in the preceding oscillating cycle.

Figure 8A:
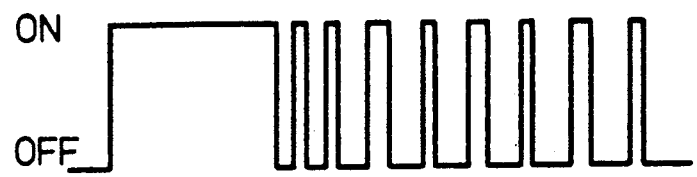
FIGS. 8(A) and 8(B) are graphs showing the manner in which a vacuum pump is turned on and off and the pressure in a vacuum blood sampling chamber.

(1) The memory 66 stores a secondary preset pressure $P_2$ lower in vacuum level than a preset reference pressure $P_1$, and the CPU 65 lowers the vacuum in the vacuum blood sampling chamber 13 from the preset reference pressure $P_1$ to the secondary preset pressure $P_2$ under the condition given in (b) above (see FIG. 8(A)).

Figure 8B:
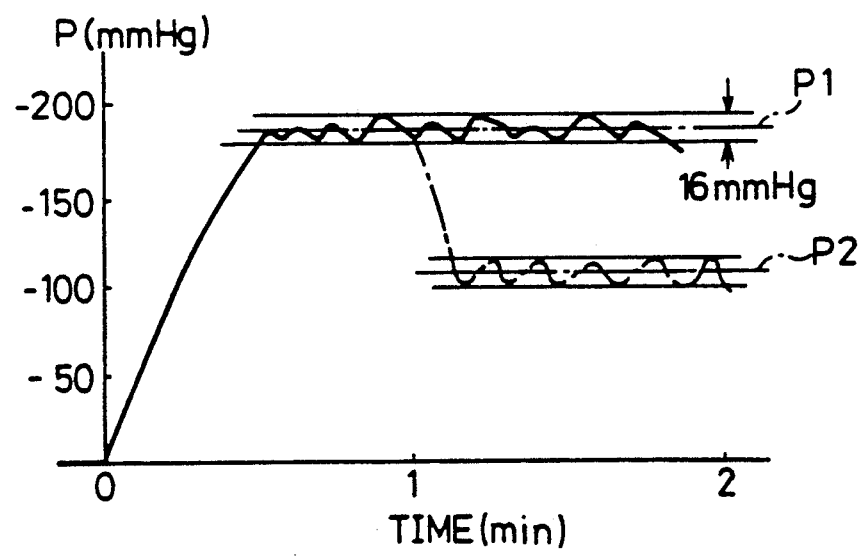

At this time, the CPU 65 opens the discharge valve 43 in the vacuum pipe 41 to reduce the vacuum in the vacuum blood sampling chamber 13 from the preset reference pressure $P_1$ to the secondary preset pressure $P_2$. In this manner, the vacuum pressure in the vacuum blood sampling chamber 13 can quickly be lowered (see FIG. 8(B)).

The CPU 65 turns on or off the vacuum pump 17 to control the vacuum in the vacuum blood sampling chamber 13 so as to reach the preset reference pressure $P_1$ or the secondary preset pressure $P_2$. Therefore, the vacuum pressure in the vacuum blood sampling chamber 13 can be controlled so as to be maintained at a constant level without having to continuously operate the vacuum pump 17, with the result that the electric efficiency of the vacuum pump 17 can be increased and the pressure can be controlled stably with respect to time.

(2) Under the condition given in (b) above, the CPU 65 may lower stepwise the vacuum pressure in the vacuum blood sampling chamber 13 from the preset pressure until the rate of increase in the amount of collected blood as measured by the scale 33 reaches the normal rate of increase.

According to the embodiment which achieves the first object of the invention, the target level for the vacuum pressure in the vacuum blood sampling chamber 13 is stored as a preset pressure in the memory 66, the actual pressure in the vacuum blood sampling chamber 13 is detected by the pressure sensor 73, and the CPU 65 controls the pressure in the vacuum blood sampling chamber 13 so that the detected pressure will coincide with the preset pressure. At the same time, the amount of collected blood in the blood bag 1 is measured, and on the condition that the rate of increase in the amount of collected blood does not reach a predetermined normal rate of increase while the detected pressure reaches the preset pressure, the CPU 65 determines that the hole of the blood sampling needle is closed by a blood vessel wall attracted thereto, and then reduces the vacuum pressure in the vacuum blood sampling chamber 13 so as to be lower than the preset pressure. Thus, the suction force applied to draw blood from the blood vessel is automatically adjusted to a level capable of sampling blood (e.g., a level capable of sampling blood of its own accord without an external pressure applied). Accordingly, irrespective of the diameter of the blood vessel from which blood is sampled, blood can stably be collected, and blood can smoothly be collected from a blood donor even if the blood vessel is thin, though a somewhat longer time may be needed to collect a desired blood sample According to the process (1) above for reducing the vacuum level, the suction force applied to collect blood can automatically be adjusted immediately to a level which is capable of sampling blood.

According to the process (2) above for reducing the vacuum level, the interval or extent by which the suction force to collect blood is lowered can be held to a minimum range required.

In this embodiment, the CPU 65 may determine that the hole of the blood sampling needle is closed by a blood vessel wall attracted thereto, and may reduce the vacuum pressure in the vacuum blood sampling chamber 13, only on the condition that the rate of increase in the amount, as measured, of collected blood in the blood bag 1 does not reach a predetermined normal rate of increase The above embodiment is widely applicable to vacuum blood sample collecting devices no matter how the amount of collected blood may be measured and the pressure in the vacuum blood sampling chamber may be regulated, and allows blood to be stably collected from blood vessels having different diameters.

An additional arrangement for achieving the second object, its operation and advantages will be described below.

Figure 9A:
FIGS. 9(A) and 9(B) are graphs showing the manner in which a vacuum pump is turned on and off and the pressure in a vacuum blood sampling chamber.
Figure 9B:
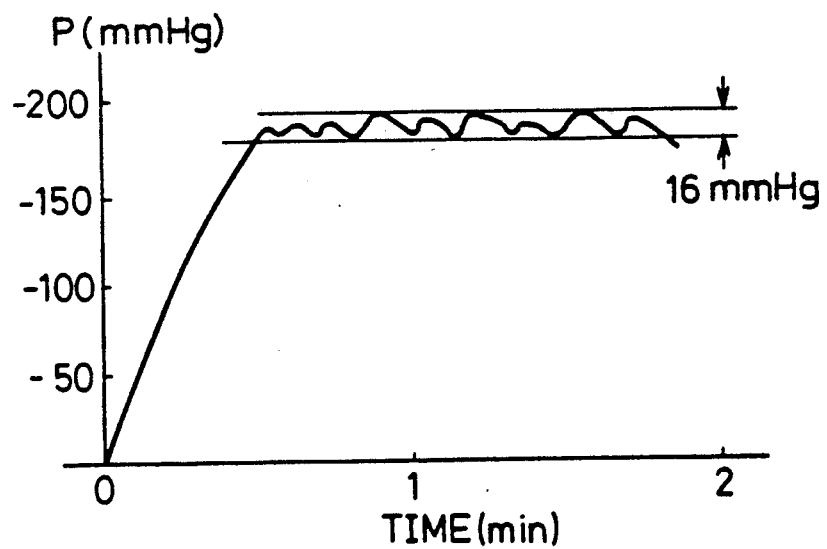

In this embodiment, a target level for the vacuum to be developed in the vacuum blood sampling chamber 13 is stored as a preset pressure in the memory 66, the actual pressure in the vacuum blood sampling chamber 13 is detected by the pressure sensor 73, and the CPU 65 turns on and off the vacuum pump 17 as shown in FIG. 9(A) so that the detected pressure will coincide with the preset pressure. The vacuum pressure in the vacuum blood sampling chamber 13 varies slightly within a constant preset pressure range, and is thus held at a substantially constant level, as shown in FIG. 9(B).

According to the embodiment designed to accomplish the second object, therefore, the vacuum pump 17 is not continuously operated, the electric efficiency thereof is increased, and the problem of undesirable heating is avoided. Even if the seal in the vacuum pipe may be deteriorated with time, the CPU 65 can develop a desired target vacuum pressure in the vacuum blood sampling chamber 13 by automatically adjusting the on- and off-times of the vacuum pump 17, and hence the pressure can be controlled stably with respect to time.

The vacuum in the vacuum blood sampling chamber 13 can easily be changed by rewriting the data stored in the memory 66. Since the memory 66 is nonvolatile, the preset pressure stored in the memory 66 is not erased even when the power supply is cut off due to a power failure, and the same preset pressure can be maintained unless the data thereof is rewritten.

An additional arrangement for achieving the third object, its operation and advantages will be described below.

According to this embodiment, a rate c of increase in the amount of blood collected in the blood bag 1 is controlled in the manner described below during the blood sampling process described above and the mode (9) for setting a rate of increase in the amount of blood is added by the selector switch 81.

The CPU 65 controls the rate $\alpha$ of increase in the amount of collected blood measured by the scale 33 while blood is being collected. The rate of increase in the amount of collected blood is indicated by a rate of increase with respect to measuring time. In this embodiment, the rate of increase in the amount of collected blood is represented as an increase in the amount of collected blood measured when the bag tray 19 reaches the lowest position in the present oscillating cycle, from the amount of collected blood measured when the bag tray 19 reaches the lowest position in the preceding oscillating cycle.

After blood starts being collected, the amount of collected blood in the blood bag 1 is measured by the scale 33, and the collection of a blood sample is continued while the rate $\alpha$ of increase in the amount of collected blood as measured is being controlled by the CPU 65.

Therefore, blood can be sampled from a blood donor at a rate $\alpha$ of increase which will not place a burden on the blood donor. Since the rate $\alpha$ of increase is controlled, the rate of increase is prevented from being reduced below a normal level due to the hole of the blood sampling needle being closed by a blood vessel wall attracted thereto, and it is not difficult or impossible to collect blood from a thin blood vessel of a blood donor. The efficiency of collecting blood is thus increased.

The rate $\alpha$ of increase in the amount of blood can be controlled in either of the following processes (A), (B), and (C):

(A) The CPU 65 continuously reduces the vacuum level in the vacuum blood sampling chamber 13 until the measured $\alpha$ of increase in the amount of collected blood goes higher than a preset rate $\alpha$ of increase. According to this control process, by setting the measured rate $\alpha$ of increase in the amount of collected blood to an appropriately preset rate $\alpha$ of increase, the burden on the blood donor can be reduced, and the efficiency of sampling blood is improved. More specifically, one of the following control processes (1) and (2) is employed:

(1) The vacuum level in the vacuum blood sampling chamber 13 is controlled to maintain a vacuum level P in the vacuum blood sampling chamber 13 when the measured rate $\alpha$ reaches the preset rate $\alpha$.

(2) The vacuum level Px in the vacuum blood sampling chamber 13 is controlled to keep the measured rate $\alpha$ as the preset rate $\alpha$.

In the process (A), the preset rate $\alpha$ is stored in the memory 66 or may be stored in a memory in the CPU 65.

(B) The CPU 65 continuously reduces the vacuum level in the vacuum blood sampling chamber 13 until the measured rate $\alpha$ reaches a saturated rate $\alpha_{max}$ which no longer varies. According to this control process, by setting a final value of the rate $\alpha$ of increase in the amount of collected blood as the saturated rate $\alpha_{max}$, the burden on the blood donor can be reduced while blood is being collected, and the efficiency of sampling blood is increased. More specifically, one of the following control processes (1) and (2) is selected:

(1) The vacuum level in the vacuum blood sampling chamber 13 is controlled to maintain a vacuum level P in the vacuum blood sampling chamber 13 when the measured rate $\alpha$ reaches the saturated rate $\alpha_{max}$.

(2) The vacuum level Px in the vacuum blood sampling chamber 13 is controlled to keep the measured rate $\alpha$ as the saturated rate $\alpha_{max}$.

Figure 10:
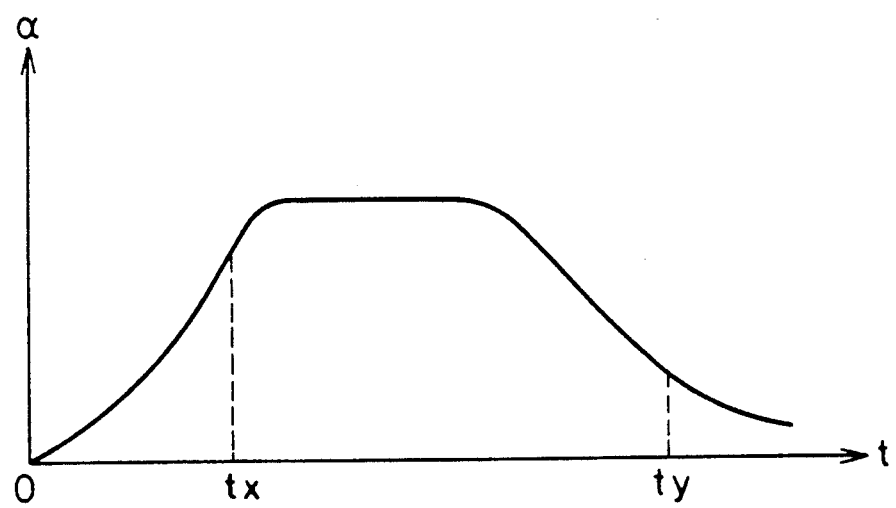
FIG. 10 is a graph showing a pattern of a rate of increase in the amount of collected blood.

(C) The CPU 65 controls the vacuum level in the vacuum blood sampling chamber 13 to allow the preset rate $\alpha$ is maintained according to a certain rate-of-increase pattern which is predetermined with respect to blood sampling time t. According to this control process, blood can be collected from a blood donor according to a certain rate-of-increase pattern which is determined in advance with a view to reducing the burden on the blood donor and increasing the blood sampling efficiency. For example, a rate-of-increase pattern shown in FIG. 10 may be employed. According to the pattern of FIG. 10, the amount of collected blood is gradually increased during an initial blood sampling period up to a time tx, thus lessening the burden on the blood donor and preventing the occurrence of hemolysis, and the amount of collected blood is gradually reduced during a final blood sampling period after a time ty, thereby increasing the accuracy of the amount of collected blood.

In each of the control processes (A), (B), and (C), the vacuum level in the vacuum blood sampling chamber 13 can be reduced stepwise or continuously with respect to time. When the vacuum level is reduced stepwise, the CPU 65 derives a measured rate $\alpha$ of increase each time the vacuum level reaches one of the pressure steps.

In each of (1) and (2) of the process (A), (1) and (2) of the process (B), and the process (C), the vacuum level in the vacuum blood sampling chamber 13 may be controlled by a) turning on and off the vacuum pump 17 or b) turning on and off or continuously controlling (in an analog manner) the pressure control valve in the vacuum pipe 41. More specifically, the power supply switch 77 of the vacuum pump 17 is turned on and off in a) above or the pressure control valve is turned on and off or continuously controlled in an analog manner in b) above so that the pressure detected by the pressure sensor 73 will be equalized to the target pressure stored in the memory 66.

According to the embodiment which is designed to accomplish the third object, therefore, when blood is collected into the blood container under the vacuum developed in the vacuum blood sampling chamber, the burden on the blood donor is reduced, and the blood sampling efficiency is increased.

This embodiment is widely applicable to vacuum blood sample collecting devices irrespective of how the amount of collected blood may be measured and the pressure in the vacuum blood sampling chamber may be regulated, and allows blood to be stably collected from blood vessels having different diameters.

Although certain preferred embodiments have been shown and described, it should be understood that many changes and modifications may be made therein without departing from the scope of the appended claims.

What is claimed is:

1. A blood sample collecting device comprising:
   a vacuum blood sampling chamber having a blood container disposed thereon;
   a vacuum pump for evacuating the vacuum blood sampling chamber to collect a blood sample into the blood container under a vacuum developed in said vacuum blood sampling chamber;
   measuring means for measuring the amount of collected blood in said blood container;
   means coupled to said measuring means for determining a rate of increase in the measured amount of collected blood; and
   control means for lowering the vacuum in said vacuum blood sampling chamber below a preset pressure when said determined rate of increase in the measured amount of collected blood is less than a predetermined normal rate of increase.

2. A blood sample collecting device according to claim 1, wherein said measuring means comprises:
   a pressure sensor for detecting the pressure in said vacuum blood sampling chamber; and
   memory means for storing the preset pressure to be developed in said vacuum blood sampling chamber, and wherein said control means comprises:
   means responsive to the pressure detected by said pressure sensor, the preset pressure stored in said memory means, and the measured amount from said measuring means, for controlling the pressure in said vacuum blood sampling chamber so that the pressure detected by said pressure sensor will coincide with the preset pressure stored in said memory means, and for lowering the vacuum in said vacuum blood sampling chamber below preset pressure under the condition that the rate of increase in the measured amount of collected blood does not reach the predetermined normal rate of increase while the pressure detected by said pressure sensor reaches the preset pressure stored in said memory means.

3. A blood sample collecting device according to claim 2, wherein said memory means comprises:
   means for storing a preset reference pressure and a secondary preset pressure lower in vacuum level than said preset reference pressure, and wherein said control means comprises:
   means for lowering the vacuum in said vacuum blood sampling chamber from said preset reference pressure to said secondary preset pressure under said condition.

4. A blood sample collecting device according to claim 1, wherein said control means comprises means for turning on and off said vacuum pump when controlling the vacuum in said vacuum blood sampling chamber so as to be equal to said preset pressure.

5. A blood sample collecting device according to claim 1, wherein said control means comprises:
means for lowering the vacuum in said vacuum blood sampling chamber stepwise from said preset pressure under said condition until said rate of increase in the measured amount reaches said normal rate of increase.

6. A blood sample collecting device according to claim 1, further including a vacuum pipe interconnecting said vacuum pump and said vacuum blood sampling chamber to each other and having a discharge valve, said control means comprising means for opening said discharge valve to lower the vacuum in said vacuum blood sampling chamber.

7. A blood sample collecting device according to claim 6, wherein said control means comprises means for lowering the vacuum level in said vacuum blood sampling chamber stepwise with respect to time in the blood collecting cycle, and deriving said rate of increase in the measured amount of collected blood each time the vacuum level reaches one of steps.

8. A blood sample collecting device comprising:
a vacuum blood sampling chamber having a blood container disposed therein;
a vacuum pump for evacuating the vacuum blood sampling chamber to collect a blood sample into the blood container under a vacuum developed in said vacuum blood sampling chamber;
a pressure sensor for detecting the pressure in said vacuum, blood sampling chamber;
memory means for storing a preset pressure to be developed in said vacuum blood sampling chamber, said memory means comprising a nonvolatile memory capable in which said preset pressure can be rewritten; and
control means responsive to the pressure detected by said pressure sensor and the preset pressure stored in said memory means for turning on and off said vacuum pump so that the pressure detected by said pressure sensor will coincide with the preset pressure stored in said memory means.

9. A blood sample collecting device comprising:
a vacuum blood sampling chamber having a blood container disposed therein;
a vacuum pump for evacuating the vacuum blood sampling chamber to collect a blood sample into the blood container under a vacuum developed in said vacuum blood sampling chamber;
measuring means for measuring the amount of collected blood in said blood container;
means coupled to said measuring means for determining a rate of increase in the measured amount of collected blood; and
control means for controlling said rate of increase in the measured amount of collected blood during a blood collecting cycle.

10. A blood sample collecting device according to claim 9, wherein said control means comprises means for lowering the vacuum level in said vacuum blood sampling chamber until said rate of increase in the measured amount of collected blood becomes higher than a predetermined rate of increase.

11. A blood sample collecting device according to claim 10, wherein said control means comprises means for controlling the vacuum level in said vacuum blood sampling means in order to maintain a vacuum level reached when said rate of increase in the measured amount of collected blood reaches said preset rate of increase.

12. A blood sample collecting device according to claim 9, wherein said control means comprises means for controlling the vacuum level in said vacuum blood sampling chamber to maintain said rate of increase in the measured amount of collected blood as said preset rate of increase.

13. A blood sample collecting device according to claim 9, wherein said control means comprises means for lowering the vacuum level in said vacuum blood sampling chamber until said rate of increase in the measured amount of collected blood reaches an invariable saturated rate of increase.

14. A blood sample collecting device according to claim 13, wherein said control means comprises means for controlling the vacuum level in said vacuum blood sampling means in order to maintain a vacuum level reached when said rate of increase in the measured amount of collected blood reaches said saturated rate of increase.

15. A blood sample collecting device according to claim 13, wherein said control means comprises means for controlling the vacuum level in said vacuum blood sampling chamber to maintain said rate of increase in the measured amount of collected blood as said saturated rate of increase.

16. A blood sample collecting device according to claim 9, wherein said control means comprises means for controlling the vacuum level in said vacuum blood sampling chamber so that the rate of increase in the measured amount of collected blood varies according to a rate-of-increase pattern predetermined with respect to time in the blood collecting cycle.

17. A blood sample collecting device according to claim 9, wherein said control means comprises means for lowering the vacuum level in said vacuum blood sampling chamber stepwise with respect to time in the blood collecting cycle, and deriving said rate of increase in the measured amount of collected blood each time the vacuum level reaches on of steps.

* * * * *

UNITED STATES PATENT AND TRADEMARK OFFICE
CERTIFICATE OF CORRECTION

PATENT NO. : 5,035,865
DATED : July 30, 1991
INVENTOR(S) : INABA et al

It is certified that error appears in the above-identified patent and that said Letters Patent is hereby corrected as shown below:

Column 2, line 45, "mean" should read --means--.

Column 10, line 25, "c" should read --α--.

Column 14, line 58 (Claim 17), "on" should read --one--.

Signed and Sealed this

Ninth Day of March, 1993

Attest:

STEPHEN G. KUNIN

Attesting Officer                Acting Commissioner of Patents and Trademarks